United States Patent [19]

Kino et al.

[11] Patent Number: 5,362,637
[45] Date of Patent: Nov. 8, 1994

[54] PROCESS FOR PRODUCING L-ISOLEUCINE AND ETHIONINE BY ISOLEUCINE ANALOG RESISTANT STRAINS OF E. COLI

[75] Inventors: Kuniki Kino; Yoshiyuki Kuratsu, both of Houhu, Japan

[73] Assignee: Kyowa Hakko Kogy Co., Ltd., Tokyo, Japan

[21] Appl. No.: 973,452

[22] Filed: Nov. 9, 1992

[30] Foreign Application Priority Data

Nov. 11, 1991 [JP] Japan .................................. 3-294420

[51] Int. Cl.$^5$ .............................................. C12P 13/06
[52] U.S. Cl. .................. 435/116; 435/252.8; 435/849
[58] Field of Search ....................... 435/116, 252.8, 849

[56] References Cited

U.S. PATENT DOCUMENTS 5,017,483  5/1991  Furukawa et al. ................... 435/115
5,087,566  2/1992  Takano et al. ........................ 435/115

FOREIGN PATENT DOCUMENTS 0213536  3/1987  European Pat. Off. .
0356739  3/1990  European Pat. Off. .
2491495  4/1982  France .
0101582  8/1975  Japan .................................. 435/116

OTHER PUBLICATIONS

Kisumi et al., "Properties of Isoluecine Hydroxamate-Resistant Mutants of Serratia marcescens", J. of Gen. Microbiol., vol. 69, pp. 291–297 1971.

Nakamura, et al., Chem. Abs, 89(17):462 (1978).
Komatsubara et al., 1980, "Transductional Construction of an Isoleucine–producing Strain of Serratia marcescens", J. Gen. Microbiol., 119:51–61.
Kisumi et al., 1977, "Enhancement of Isoleucine Hydroxamate-Mediated Growth Inhibition and Improvement of Isoleucine-Producing Strains of Serratia marcescens", App. and Environ. Microbiol., 34(6):647–653.
Kase and Nakayama, 1977, "L–Isoleucine Production by Analog-resistant Mutants Derived from Threonine-producing Strain of Corynebacterium glutamicum", Agric. Biol. Chem., 41(1):109–116.
Ikeda et al., 1976, "Screening of L–Isoleucine Producers among Ethionine Resistant Mutants of L–Threonine Producing Bacteria", Agr. Biol. Chem., 40(3):511–516.
Kisumi et al., 1972, "Isoleucine Accumulation by Regulatory Mutants of Serratia marcescens: Lack of Both Feedback Inhibition and Repression", J. Bacteriol., 110(2):761–763.
Szentirmai et al., 1968, "Isoleucine and Valine Metabolism of Escherichia coli", J. Bacteriology 95(5):1672–1679.

Primary Examiner—Marian Knode
Attorney, Agent, or Firm—Pennie & Edmonds

[57] ABSTRACT

Disclosed is a process for producing L-isoleucine which comprises culturing in a medium a microorganism belonging to the genus Escherichia and having resistance to an isoleucine analogue and either ethionine or argonine hydroxamate and an ability to produce L-isoleucine until L-isoleucine is accumulated in the culture, and recovering L-isoleucine therefrom.

2 Claims, No Drawings

PROCESS FOR PRODUCING L-ISOLEUCINE AND ETHIONINE BY ISOLEUCINE ANALOG RESISTANT STRAINS OF E. COLI

INTRODUCTION

The present invention relates to a process for producing L-isoleucine. L-isoleucine, one of the essential amino acids, plays a nutritiously important role for humans and animals and is used for medicaments such as amino acid preparations, food, and animal feeds. Demand for L-isoleucine has been steadily increased in recent years.

BACKGROUND OF THE INVENTION

As four optical isomers are known against isoleucine, it is difficult to produce L-isoleucine alone at a low cost by processes using chemical synthesis or a combination of chemical synthesis and enzymatic partition. Therefore, industrial production of L-isoleucine is mainly carried out by fermentation.

Various processes for producing L-isoleucine by fermentation are known. For example, it is known to add an L-isoleucine-precursor, such as DL-α-aminobutyric acid, α-ketobutyric acid, or threonine, to a fermentation medium or a microbial reaction system to convert the precursor to L-isoleucine. This method is known as a precursor addition method (Japanese Published Examined Patent Application Nos. 45347/60, 7091/63, 8709/68, 29789/71). However, the method is unsuitable for industrial production of L-isoleucine because of the need of expensive materials, the low yield and the unstability of the precursors.

On the other hand, as indirect fermentation methods, there are known a process by the use of microorganism belonging to *Serratia marcescens* having resistance to α-aminobutyric acid and isoleucine hydroxamate (J. Bacteriology, 110:761–763, 1972; Applied and Environmental Microbiology, 34: 647–653, 1977), a process by the use of a microorganism belonging to the genus *Brevibacterium* having resistance to α-amino-β-hydroxyvaleric acid and o-methylthreonine (Japanese Published Unexamined Patent Application No. 93586/74), a process by the use of a microorganism belonging to the genus *Corynebacterium* having sensitivity to fluoropyruvic acid (Japanese Published Examined Patent Application No. 60236/89). Furthermore, there are known a process by the use of a microorganism belonging to *Serratia marcescens* which is improved by a combination of mutation and transduction (J. General Microbiology, 119:51–61, 1980), a process by the use of a microorganism belonging to the genus *Escherichia* or *Brevibacterium* which is increased activity of threonine deaminase or acetohydroxy acid synthase, key enzymes of synthesizing L-isoleucine, by using recombinant DNA technology (Japanese Published unexamined Patent Application Nos. 458/90, 42988/90).

SUMMARY OF THE INVENTION

The present invention provides a process for producing L-isoleucine which comprises culturing in a medium a microorganism belonging to the genus *Escherichia* and having resistance to an isoleucine analogue and an ability to produce L-isoleucine until L-isoleucine is accumulated in the culture, and recovering L-isoleucine therefrom.

DETAILED DESCRIPTION OF THE INVENTION

As the microorganism used in the present invention, any microorganism may be used so long as it belongs to the genus *Escherichia*, and has resistance to an isoleucine analogue and an ability to produce L-isoleucine. An isoleucine analogue used in the present invention includes thiaisoleucine and isoleucine hydroxamate. Microorganism may have resistance to arginine hydroxamate and/or ethionine as well as isoleucine analogue.

The suitable mutant strains to be used of the present invention can be obtained by endowing the resistance to an isoleucine analogue such as thiaisoleucine or isoleucine hydroxamate, optionally with the resistance to arginine hydroxamate and/or ethionine to an L-threonine-producing microorganism belonging to the genus *Escherichia* by a conventional mutation technique. Alternatively, the mutant strains can be also obtained by a reverse process, i.e. by imparting L-isoleucine-productivity such as endowment of nutrient requirement or threonine metabolic antagonist resistance to mutant strains having the isoleucine analogue-resistance, optionally with arginine hydroxamate and/or ethionine-resistance derived from a wild strain belonging to the genus *Escherichia*. Specific examples of the L-isoleucine-producing microorganism include *Escherichia coli* H-8271, *Escherichia coli* H-8272, *Escherichia coli* H-8273, *Escherichia coli* H-8285 and *Escherichia coli* H-8362.

According to the present invention, production of L-isoleucine can be effected by culturing the microorganism in a conventional manner. As the medium used, any synthetic or natural medium may be used so long as it appropriately contains carbon sources, nitrogen sources, inorganic compounds and trace amounts of other nutrients required for the strain used.

As the carbon sources, carbohydrates such as glucose, fructose, lactose, molasses, cellulose hydrolyzate, crude sugar hydrolyzate, starch hydrolyzate, etc.; and organic acids such as pyruvic acid, acetic acid, fumaric acid, malic acid, lactic acid, etc. can be used. Depending upon assimilability of a microorganism to be used, alcohols such as glycerol, ethanol, etc. may also be used.

As the nitrogen sources, ammonia; various inorganic and organic ammonium salts such as ammonium chloride, ammonium sulfate, ammonium acetate, ammonium phosphate, etc.; amine and other nitrogen-containing compounds, peptone, meat extract, corn steep liquor, casein hydrolyzate, soybean cake hydrolyzate, various fermented cells or their digested product, etc. can be used.

As the inorganic compounds, potassium dihydrogen phosphate, dipotassium hydrogen phosphate, magnesium phosphate, magnesium sulfate, sodium chloride, ferrous sulfate, manganese sulfate, copper sulfate, calcium carbonate, etc. can be used.

Culturing is carried out under aerobic conditions, for example, by submerged shaking culture and aeration-agitation culture. The temperature for the culturing is in a range of 20°–40° C., preferably 25°–38° C. The pH of the medium is in a range of 5–9, preferably maintained around neutrality. During the culturing, the pH of the medium is adjusted by using calcium carbonate, inorganic and organic acids, alkali solution, ammonia, pH buffer, etc. Usually, by culturing for 2–7 days, L-isoleucine is formed and accumulated in the culture.

After the completion of culturing, precipitates such as cells, etc. are removed from the culture and L-isoleucine can be recovered from a supernatant by a combination of a technique such as a treatment with ion-exchange, concentration and salting-out, etc.

Hereafter the present invention is specifically described with reference to the examples.

EXAMPLE 1

Acquirement of the mutant strain of the present invention

*Escherichia coli* H-4258(FERM BP-985; diaminopimeric acid requirement, methionin requirement, α-amino-β-hydroxyvaleric acid resistance, rifampicin resistance) was treated with N-methyl-N'-nitro-N-nitrosoguanidine (0.2 mg/ml) at 30° C. for 30 minutes to effect mutation by a conventional method. The cells were spread on a medium containing 1 g/l thiaisoleucine in a minimum medium/pH 7.2 (0.5% glucose, 0.2% $NH_4Cl$, 0.2% $KH_2PO_4$, 0.01% $MgSO_4 \cdot 7H_2O$, 20 mg/l $FeSO_4 \cdot 7H_2O$, 50 mg/l DL-methionine, 200 mg/l diaminopimeric acid, 2% agar). After culturing at 30° C. for 2-6 days, large colonies grown on the medium, thiaisoleucine-resistant mutants, were picked up and subjected to the L-isoleucine production test. A mutant having a higher L-isoleucine productivity than that of *Escherichia coli* H-4258 was selected. Thus, *Escherichia coli* H-8271 was obtained.

*Escherichia coli*; H-8271 was deposited with Fermentation Research Institute, Agency of Industrial Science and Technology 1-3, Higashi 1-chome, Tsukuba-shi, Ibaraki-ken, 305 Japan on Oct. 29, 1991, under the Budapest treaty, with the accession No. FERM BP-3626.

The same procedure as in the acquirement of the thiaisoleucine-resistant mutant was repeated except that 1.5 g/l isoleucine hydroxamate was contained in the medium in place of 1 g/l thiaisoleucine. Thus, *Escherichia coli* H-8272 was obtained.

*Escherichia coli* H-8272 was deposited with Fermentation Research Institute, Agency of Industrial Science and Technology, on Oct. 29, 1991, under the Budapest treaty, with the accession No. FERM BP-3627.

Thiaisoleucine-resistant mutant H-8271 was further subjected to mutation treatment in the same manner as described above and then, the cells were spread on a medium containing 0.3 g/l arginine hydroxamate in a minimum medium. After culturing at 30° C. for 2-6 days, large colonies grown on the medium, arginine hydroxamate-resistant mutants, were picked up and subjected to the L-isoleucine production test. A mutant having a higher L-isoleucine productivity than that of *Escherichia coli* H-8271 was selected. Thus, *Escherichia coli* H-8273 was obtained.

*Escherichia coli* H-8273 was deposited with Fermentation Research Institute, Agency of Industrial Science and Technology, on Oct. 29, 1991, under the Budapest treaty, with the accession No. FERM BP-3628.

Thiaisoleucine-resistant mutant H-8271 and arginine hydroxamate-resistant mutant H-8273 were further subjected to mutation treatment in the same manner as described above and then, the cells were spread on a medium containing 10 g/l DL-ethionine in a minimum medium, respectively. After culturing at 30° C. for 2-6 days, large colonies grown on the medium, DL-ethionine-resistant mutants, were picked up and subjected to the L-isoleucine production test. Mutants having a higher L-isoleucine productivity than that of *Escherichia coli* H-8271 and *Escherichia coli* H-8273 were selected, respectively. Thus, *Escherichia coli* H-8362 and *Escherichia coli* H-8285 were obtained.

*Escherichia coli* H-8362 and *Escherichia coli* H-8285 were deposited with Fermentation Research Institute, Agency of Industrial Science and Technology, on Oct. 29, 1991, under the Budapest treaty, with the accession Nos. FERM BP-3630 and FERM BP-3629, respectively.

The thus obtained mutants were compared with their respective parent strains with respect to the resistance to thiaisoleucine, isoleucine hydroxamate, arginine hydroxamate or DL-ethionine. That is, each strain was cultured in a medium/pH 7.5 (1% trypton, 0.5% yeast extract, 1% NaCl, 200mg/l diaminopimelic acid) for 24 hours. The cells were then suspended in a sterilized water and the suspensions were spread on a minimum medium containing thiaisoleucine, isoleucine hydroxamate, arginine hydroxamate, or DL-ethionine in the amounts shown in Table 1. After culturing at 30° C. for 72 hours, drug resistance was determined by the degree of growth. The results are shown in Table 1.

TABLE 1

| strain | thiaisoleucine (g/l) | | |
|---|---|---|---|
| | 0 | 0.3 | 1 |
| H-4258 | + | ± | − |
| H-8271 | + | + | + |
| H-8362 | + | + | + |
| H-8273 | + | + | + |
| H-8285 | + | + | + |
| | isoleucine hydroxamate (g/l) | | |
| | 0 | 0.5 | 1.5 |
| H-4258 | + | ± | − |
| H-8272 | + | + | + |
| H-8271 | + | + | + |
| | arginine hydroxamate (g/l) | | |
| | 0 | 0.1 | 0.3 |
| H-8271 | + | ± | − |
| H-8273 | + | + | + |
| H-8285 | + | + | + |
| | DL-ethionine (g/l) | | |
| | 0 | 5 | 10 |
| H-8271 | + | ± | − |
| H-8362 | + | + | + |
| H-8273 | + | ± | − |
| H-8285 | + | + | + |

+: sufficient growth
±: slight growth
−: no growth

EXAMPLE 2

L-isoleucine production test (1)

*Escherichia coli* H-8271, *Escherichia coli* H-8272, *Escherichia coli* H-8273, *Escherichia coli* H-8362 and *Escherichia coli* H-8285 obtained in Example 1 and *Escherichia coli* H-4258 were cultured with shaking at 30° C. for 16 hours in a seed medium/pH 7.4 comprising 2% glucose, 1% peptone, 1% yeast extract, 0.25% NaCl, 200mg/l diaminopimelic acid, respectively. Then, 0.5 ml of the resulting seed culture was inoculated into 20 ml of a fermentation medium/pH 8.0 (6% glucose, 1.6% ammonium sulfate, 0.1% potassium dihydrogen phosphate, 100mg/l DL-methionine, 300 mg/l diaminopimelic acid, 0.2% corn steep liquor, 4% magnesium phosphate, 1% calcium carbonate) charged in a 300-ml edenmeyer flask and cultured with shaking at 30° C. for 72 hours. After the completion of the culturing, the amounts of L-isoleucine and L-threonine accumulated was quantitatively analyzed by high performance liquid chromatography. The results are shown in Table 2.

TABLE 2

| strain | L-isoleucine (g/l) | L-threonine (g/l) |
| --- | --- | --- |
| H-4258 | 0 | 15.2 |
| H-8271 | 2.7 | 12.7 |
| H-8272 | 2.3 | 12.9 |
| H-8362 | 5.8 | 3.0 |
| H-8273 | 9.2 | 2.3 |
| H-8285 | 12.5 | 0.2 |

EXAMPLE 3

L-isoleucine production test (2)

The resulting seed culture (100ml) of *Escherichia coli* H-8285 obtained in Example 2 was inoculated into I liter of a fermentation medium/pH 7.4 (4% glucose, 0.5 % $(NH_4)_2SO_4$, 0.1% $KH_2PO_4$, 0.01% $MgSO_4 \cdot 7H_2O$, 0.5 % corn steep liquor, 0.35 g/l DL-methionine, 0.9 g/l diaminopimelic acid) charged in a 2-liter fermentation tank and cultured with shaking (at 800 rpm) at 30 ° C., at an aeration rate of 1 liter/min. During the culturing, aqueous ammonia was added to the culture to adjust the pH to 6.5±0.2 and supply a nitrogen source. Glucose was also added to the culture if it is necessary. The culture was carried out for 45 hours. After the completion of the culturing, 26 mg/ml of L-isoleucine was accumulated.

One liter of the L-isoleucine-containing fermentation broth obtained by culturing H-8285 strain described above was centrifuged at 3,000 rpm for 10 minutes to remove the cells and other impurities. The obtained supernatant was passed through a column packed with strongly acidic cation exchange resin Diaion SK1B ($H^+$ type) to adsorb L-isoleucine thereto. After the column was washed with water, the column was eluted with 0.5 N aqueous ammonia. L-isoleucine fractions were collected, concentrated, and stored in ethanol under cooling. Thus, 19.3 g of L-isoleucine crystals (purity: 98% or more) was obtained.

What is claimed is:

1. A process for producing L-isoleucine which comprises culturing in a nutrient medium a microorganism having resistance to isoleucine analog and ethionine which is selected from the group consisting of *Escherichia coli* FERM BP-3629 and *Escherichia coli* FERM BP-3630 until L-isoleucine is accumulated in the culture, and recovering L-isoleucine therefrom.

2. A process for producing L-isoleucine which comprises culturing in a nutrient medium *Escherichia coli* FERM BP-3628 having resistance to thiaisoleucine and arginine hydroxamate until L-isoleucine is accumulated in the culture, and recovering L-isoleucine therefrom.

* * * * *